(12) United States Patent
Anslyn et al.

(10) Patent No.: US 9,116,147 B2
(45) Date of Patent: Aug. 25, 2015

(54) COMPOSITIONS AND METHODS FOR DETECTION OF SMALL MOLECULES USING DYES DERIVATIZED WITH ANALYTE RESPONSIVE RECEPTORS IN A CHEMILUMINESCENT ASSAY

(75) Inventors: Eric V. Anslyn, Austin, TX (US); Himali Hewage, Austin, TX (US); Ronald Houk, Austin, TX (US); Damon V. Borich, Austin, TX (US); Robert E. Hanes, Jr., Austin, TX (US); Jason A. Neeser, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 792 days.

(21) Appl. No.: 12/395,973

(22) Filed: Mar. 2, 2009

(65) Prior Publication Data

US 2009/0269765 A1 Oct. 29, 2009

Related U.S. Application Data

(60) Provisional application No. 61/032,180, filed on Feb. 28, 2008.

(51) Int. Cl.
| | | |
|---|---|---|
| C09K 3/00 | (2006.01) | |
| G01N 31/22 | (2006.01) | |
| G01N 33/53 | (2006.01) | |
| G01N 33/542 | (2006.01) | |
| G01N 21/64 | (2006.01) | |

(52) U.S. Cl.
CPC ...... *G01N 33/542* (2013.01); *G01N 2021/6432* (2013.01)

(58) Field of Classification Search
CPC ......... G01N 33/542; G01N 21/76; C12Q 1/68
USPC .............................. 250/700; 422/430; 435/7.1
See application file for complete search history.

(56) References Cited

U.S. PATENT DOCUMENTS

| | | | | |
|---|---|---|---|---|
| 5,121,302 | A * | 6/1992 | Bay et al. ......................... | 362/34 |
| 5,332,662 | A * | 7/1994 | Ullman ............................ | 435/28 |
| 6,037,130 | A * | 3/2000 | Tyagi et al. ................... | 435/6.11 |
| 6,660,532 | B1 * | 12/2003 | Lopez et al. .................. | 436/518 |
| 2003/0148257 | A1 | 8/2003 | Berkowitz et al. | |
| 2006/0029978 | A1 | 2/2006 | O'Neill et al. | |
| 2006/0046278 | A1 | 3/2006 | Ansede et al. | |
| 2006/0228256 | A1 | 10/2006 | McDevitt et al. | |
| 2007/0134747 | A1 * | 6/2007 | DiGiammarino et al. ... | 435/7.92 |

OTHER PUBLICATIONS

Huttunen et al, Novel cyclic phosphate prodrug approach for cytochrome P450 activated drugs containing alcohol functionality, 2007, Phramaceutical Research, 24, 679-687.*
Williams III et al, Evaluation of Peroxyoxalate Chemiluminescence for Determination of Enzyme Generated Peroxide, 1976, Analytical Chemistry, 48, 1003-1006.*
Wiskur et al, Teaching Old Indicators New Tricks, 2001, Acc. Chem. Res., 34, 963-972.*
Amatatongchai et al, A microfluidic system for evaluation of antioxidant capacity based on a peroxyoxalate chemiluminescence assay, 2007, Anal Bioanal Chem., 387, 277-285.*
Houk et al, Luminescent assays for ketones and aldehydes employing catalytic signal amplification, 2007, New Journal of Chemistry,31, 729-735.*
Park et al, 2006, Micromachined Chemiluminescent System for Explosives Detection, 2006, Proc. ofSPIE, 6398, R1-R11.*
Park et al, 2007, Micromachined Microfludic Chemiluminescent System for Explosives Detection, 2007, Proc. ofSPIE, 6554, 1-8.*
Hewage et al, Novel chemiluminescent detection of chemical warfare simulant, Chem. Commun., 3909-3911, published on Aug. 8, 2007.*
International Preliminary Report on Patentability for PCT/US2009/035700 dated Nov. 2, 2009.
International Search Report and Written Opinion for PCT/US09/35700, dated Nov. 2, 2009.

* cited by examiner

*Primary Examiner* — Narayan Bhat
(74) *Attorney, Agent, or Firm* — Baker Botts L.L.P.

(57) ABSTRACT

Compositions, methods, and systems for detecting small molecules using chemiluminescent signaling assay technology are provided. One system provided herein comprises a chromophore; an oxalate ester, a peroxide, and a modulating agent, wherein the modulating agent will perturb a chemiluminescent signal generated by an interaction among the chromophore, the oxalate ester, and a peroxide; and the perturbation will occur in response to an analyte. One method provided herein comprises combining a chromophore, an oxalate ester, a peroxide, and a modulating agent, wherein: the modulating agent will perturb a chemiluminescent signal generate by an interaction among the chromophore, the oxalate ester, and a peroxide; and the perturbation will occur in response to an analyte. Another method provides a colorimetric or fluorometric signal response in the presence of an analyte.

4 Claims, 3 Drawing Sheets

COMPOSITIONS AND METHODS FOR DETECTION OF SMALL MOLECULES USING DYES DERIVATIZED WITH ANALYTE RESPONSIVE RECEPTORS IN A CHEMILUMINESCENT ASSAY

CROSS-REFERENCE TO RELATED APPLICATIONS

This application claims the benefit of U.S. Provisional Patent Application Ser. No. 61/032,180, filed Feb. 28, 2008, the entire disclosure of which is incorporated by reference.

STATEMENT OF GOVERNMENT INTEREST

This invention was made with support under Grant Number 0317032 awarded by the National Science Foundation. The U.S. government has certain rights in the invention.

BACKGROUND

The field of diagnostics related to biochemical assays for the detection of chemicals, antigens and antibodies, biological species, metabolites, and related analytes has steadily advanced over the past decade. These advances are most notably in the area of medical diagnostics where a push towards more rapid and sensitive assays is the primary focus. As such, multiple novel technologies have blossomed including direct DNA and RNA detection, viral and bacterial identification, and novel reagents to assay for previously unknown biomarkers. Despite these advances, there still remains a gap between analyte detection and signaling of the detection event. Most assays still require a secondary step after binding of the analyte in order to signal that the event has occurred. This is commonly accomplished through the use of secondary reagents and visualization steps. Although these reagents are well known they do not fully address the need for an integrated detection and signaling method. As such, the present invention describes a method by which molecular recognition techniques may be coupled to existing dyes and signaling reagents in a fashion such that the signaling reagents have intrinsic detection and reporting capabilities.

The field of dye chemistry and in particular the use of dyes in chemical assays has been around for several centuries. In general, these dyes have been part of a multi-part chemical reaction or cascade whereby the dye responds indirectly to an upstream binding event. For example, in a typical glucose detection assay, glucose must first be oxidized by the enzyme glucose oxidase to yield gluconic acid and hydrogen peroxide. The byproduct hydrogen peroxide then reacts with a dye molecule to produce a visible color change. A typical glucose reaction involving the dye TMB (tetramethylbenzidine) which is oxidized by hydrogen peroxide in the presence of a peroxidase to induce a color change is shown:

Glucose Oxidase

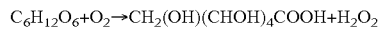

Peroxidase

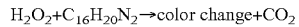

Additionally the high amounts of hydrogen peroxide produced by glucose require complimentary levels of dye which can lead to high optical density and quantitative difficulties.

A wide variety of naturally occurring and synthetically derived dyes are available and are used in applications ranging from textiles to simple colorants. Certain classes of dyes have been exploited in diagnostics due to their intrinsic ability to respond to particular conditions of their molecular environment such as pH, temperature, hydration, solvent polarity etc. A select group of these dyes in fact have the ability to bind small molecules and ions including cations such as Na, K, Cu, Zn, etc. Chrome Azurol S binds with Cu to form a blue complex, for example. Anions ranging from small organic molecules to halides such as fluoride may also be complexed. For example, alizarin complex one is known to complex fluoride. However, dyes with intrinsic capabilities to respond to complex analytes in general do not exist or are limited in their scope and/or use.

The field of molecular chemistry and in particular supramolecular recognition is a relatively new addition to the established diagnostics community. Molecular recognition involves the rational design of complementary receptor complexes that are uniquely designed to bind a pre-determined analyte or chemical species. These receptors can be designed in a manner to bind a variety of analytes ranging from simple cations and anions to larger proteins, metabolites, chemical compounds, etc. Nevertheless, despite advances in molecular recognition, the use of a signaling reagent is still needed to visualize or report the binding/detection event.

SUMMARY

The present disclosure, according to certain embodiments, provides methods comprising: combining one or more of a chromophore, an oxalate ester, a peroxide, and a modulating agent; wherein the modulating agent will perturb a chemiluminescent signal generated by an interaction among the chromophore, the oxalate ester, and the peroxide; and wherein the perturbation will occur in response to an analyte.

The present disclosure, according to certain embodiments, also provides compositions comprising a chromophore, a synthetic receptor, and an analyte, wherein the synthetic receptor is covalently coupled to the chromophore.

The present disclosure, according to certain embodiments, also provides compositions comprising a chromophore, a synthetic receptor, and an organic scaffold electronically coupling the receptor to the chromophore.

The present disclosure, according to certain embodiments, also provides compositions comprising a chromophore, an oxalate ester, a modulating agent; optionally a peroxide; and optionally an analyte; wherein the modulating agent will perturb a chemiluminescent signal generated by an interaction among the chromophore, the oxalate ester, and when present a peroxide; and wherein the perturbation will occur in response to an analyte, when present.

The features and advantages of the present invention will be readily apparent to those skilled in the art upon a reading of the description of the embodiments that follows.

DRAWINGS

A more complete understanding of this disclosure may be acquired by referring to the following description taken in combination with the accompanying figures in which.

Figure 1:
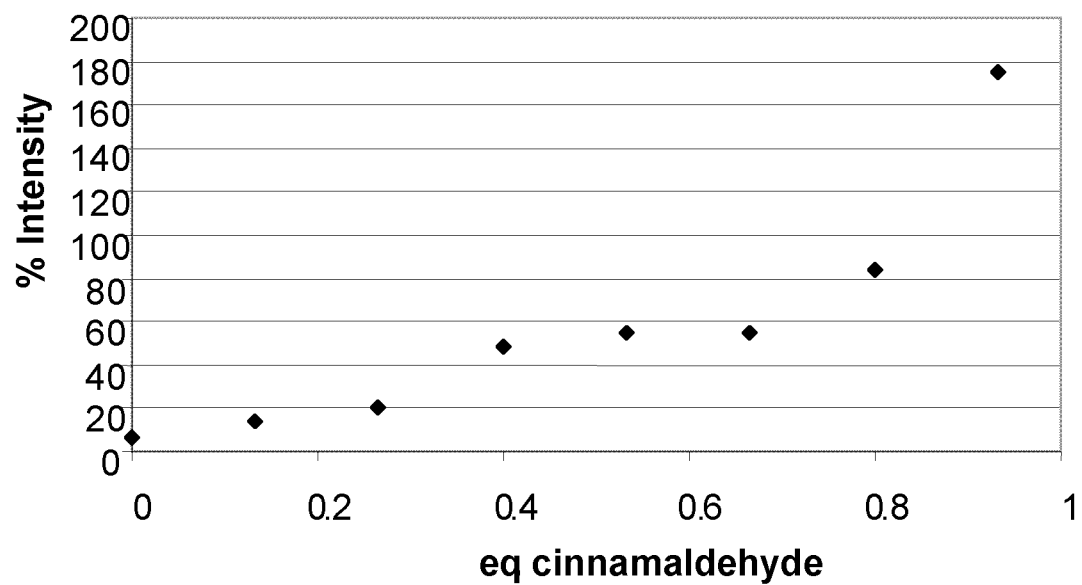
FIG. 1 depicts the rate profile of the fluorescence increase after a 120 minute reaction time for the palladium catalyzed generation of a chromophore.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The novel combination of unique molecular recognition receptors with existing dyes in a fashion such that the dye gains the capability to modulate internally its emission profile is one aspect of the present invention. By combining highly complex molecular recognition scaffolds with existing and novel dye compounds synthetically, the ability to create a wide range of analyte responsive dye reagents is possible. These compounds may then be used to directly bind, detect, and report via colorimetric, fluorescent, or chemiluminescent methods the presence or absence of a particular analyte.

As is well known, the change in absorbance spectrum, as may be measured by a common UV/vis or the human eye is most often brought about through a change in the electronic distribution of a given molecule. The absence or presence of ions is the most common method for achieving such an effect, but has also been demonstrated with small, charged organic molecules. Perturbation of the molecules electronic structure may also occur through changing the dielectric constant of the medium of the dye. Such shifts in color are caused by a change in the polarity of the medium. Indigo carmine is a dye that is known to undergo spectral changes by changing to a hydrophobic environment.

In order to demonstrate one embodiment of the current invention a common chemiluminescent reaction is described. This well known example of chemiluminescence (CL) is the peroxyoxalate chemiluminescence (POCL) found in glow sticks and necklaces that are popular in amusement parks. The POCL mechanism is outlined in Scheme 1 below. First, hydrogen peroxide reacts with the oxalate to form a peroxyoxalate intermediate, which then undergoes an intramolecular cyclization with the displacement of second phenolic group resulting in a four-membered-ring, dioxetanedione. This is the key intermediate in the POCL reaction. In the next step, the dioxetanedione undergoes a Chemically Initiated Electron Exchange Luminescence (CIEEL) mechanism, whereby an electron is transferred between a fluorophore or dye molecule, such as 9,10-diphenyl anthracene (DPA), and the dioxetanedione resulting in a radical cation fluorophore (DPA*) and a radical anion dioxetanedione. Dioxetanedione then fragments to form a $CO_2$ molecule and a $.CO_2^-$ radical anion, which then reacts with the radical cation fluorophore to yield light (hv).

Scheme 1. Chemically Initiated Electron Exchange Luminescence.

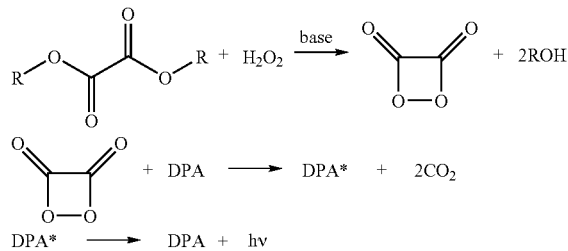

As in lithography and computer engineering, the push in molecular recognition is smaller, smaller, smaller. As the concentration of an analyte decreases however, new methods of detection must be developed. There are several mechanisms which can set the limit of detection for molecular sensing applications, such as the low binding constants or insufficient signal strength. For cases involving the latter, one way to circumvent the problem is by incorporating a catalytic process into the sensing motif to greatly amplify the signal output. While common in bio-based assays (e.g., ELISA, PCR), transition metal catalysts have only recently begun to be exploited for this purpose.

In certain embodiments, the present disclosure utilizes the POCL mechanism in a chemiluminescent assay pathway to detect the presence or absence of small molecules by modulating the chemiluminescent pathway. In general, the present disclosure provides methods wherein a chromophore, an oxalate ester, a peroxide, and a modulating agent are combined for the chemiluminescent detection of an analyte.

The chromophore may be any chromophore suitable for POCL chemiluminescence. Such chromophores are well known in the art, and include, for example: Rubrene (5,6,11,12-tetraphenylnaphthacene); 9,10 bis(phenylethynyl)anthracene; 1,8-dichloro-9,10 bis(phenylethynyl)anthracene; anthracene and anthracene derivatives; and any other luminescent chromophores.

The oxalate ester may be any oxalate ester suitable for POCL chemiluminescence. Such oxalate esters are well known in the art, for example: bis(2-carboxypentyl oxy-3,5,6 trichlorophenyl)oxalate; bis(2,4,6-trichlorophenyl)oxalate; bis(pentafluorophenyl)oxalate; bis(2,4-dinitrophenyl)oxalate; bis(2,4,6-trinitrophenyl)oxalate.

The oxalate ester may be independent of the chromophore or associated with a chromophore as an oxalate ester of the chromophore or as an oxime derivative of a chromophore.

The peroxide may be any peroxide suitable for POCL chemiluminescence. Examples of suitable peroxides include 2,4-Pentanedione peroxide (Luperox® 224) solution, 2-Butanone peroxide, Ammonium persulfate, Barium peroxide, Benzoyl peroxide, Calcium peroxide, Dicumyl peroxide, Di-tert-amyl peroxide (Luperox® DTA®), Hydrogen Peroxide Concentrate, Hydrogen peroxide solution, Hydrogen peroxide-Urea adduct, Lauroyl peroxide (Luperox® LP), Lithium peroxide, Magnesium peroxide complex, Magnesium peroxide light, Nickel peroxide, Nickel(II) peroxide hydrate, OXONE® tetrabutylammonium salt, Phosphate-Citrate Buffer with Sodium Perborate, Phosphate-Citrate Buffer with Urea Hydrogen Peroxide, Potassium peroxodisulfate, Potassium persulfate, Sodium perborate monohydrate, Sodium perborate tetrahydrate, Sodium peroxide, Sodium persulfate, Strontium peroxide, tert-Butyl hydroperoxide solution, tert-Butyl peroxide (Luperox® DI), Urea hydrogen peroxide, and Zinc peroxide.

In certain embodiments, the peroxide may be generated by an enzyme. For example, an enzyme that produces a peroxide when exposed to an analyte. For example, xanthine oxidase may be used to generate hydrogen peroxide upon exposure to caffeine, which may serve as an analyte. Another example is alcohol oxidase, which similarly generates hydrogen peroxide. These enzymes are part of the class called oxidoreductases, and one skilled in the art would recognize enzymes that generate a peroxide could be employed for this purpose.

In certain embodiments, use of an enzyme to generate a peroxide serves as the modulator. In such embodiments, the enzyme is sensitive to an analyte and the CL is modulated by the formation of peroxide, or lack thereof, based on the presence or absence of the analyte.

Any analyte that may be detected with the POCL chemiluminescence of the present disclosure is contemplated. In certain embodiments, suitable analytes may be electrophilic. For example, suitable analyte include those that having an electrophilic carbonyl group or phosphate ester group, such as the chemical warfare agents sarin and soman, as well as adenosine tri- and diphosphate (ATP and ADP). In other embodiments, suitable analytes may be analytes capable of inducing peroxide formation by an enzyme capable of producing a peroxide.

The light output from the POCL chemiluminescence of the present disclosure may be modulated in several different ways. In certain embodiments, a modulating agent may trap the oxalate ester in the absence of an analyte, thereby preventing the POCL mechanism from producing light (Scheme 2). In the presence of an analyte, the modulating agent may preferentially interact with an analyte, thereby leaving the oxalate ester untrapped, which may allow the POCL mechanism to produce an emission of light that signals the presence of an analyte (Scheme 3). This approach may be used, for example, in a signaling assay for the detection of sarin and soman chemical warfare agents (CWA).

Scheme 2. In the absence of an analyte chemiluminescence does not occur.

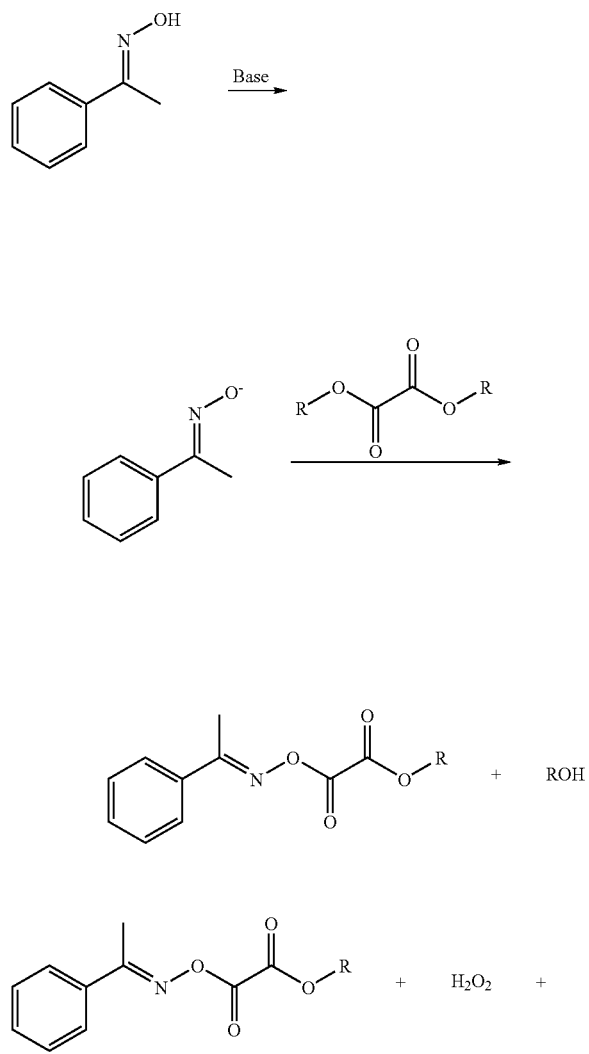

Scheme 3. Observe CL in the presence of sarin gas.

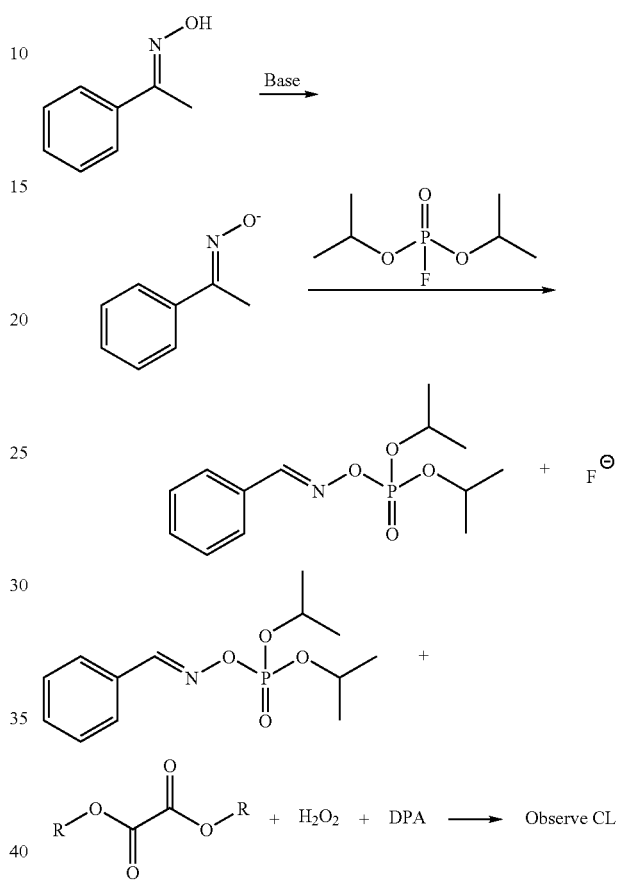

In certain embodiments, the POCL chemiluminescence of the present disclosure may be modulated using a synthetic receptor coupled to a chromophore itself, wherein the receptor and subsequent binding of an analyte to the receptor modulates the chromophore's (dye's) emission and absorbance spectrum directly. Although the examples provided pertain to a unique chemiluminescent pathway and associated fluorophore, the binding of a synthetic receptor to a chromophore may be utilized as a stand alone assay for colorimetric and fluorescent detection methods. In this manner, for example, a receptor coupled to a dye may respond to a binding event by changing color (e.g., from red to green).

In another embodiment, the modulating agent may be formed by attaching a receptor to any of the three components (chromophore, oxalate ester, hydrogen peroxide), wherein the receptor modulates one of the other components. For example, a receptor—for oxime functionality—may be incorporated on a chromophore, such as DPA, (compound 1 below) to react with an analyte. In the absence of an analyte, a receptor such as oximate reacts with the oxalate ester to perturb the chemiluminescent signal. This perturbation may change the emission wavelength and/or give rise to a visible color change.

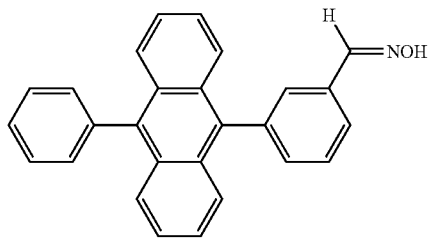

1

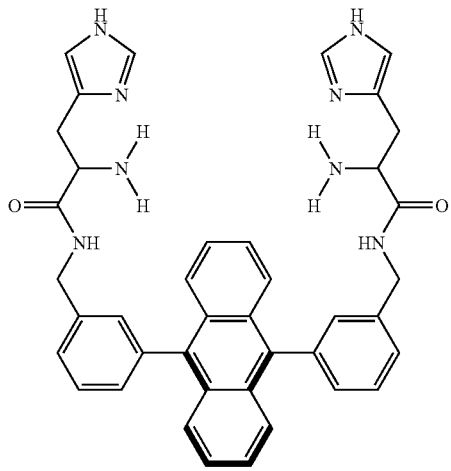

2

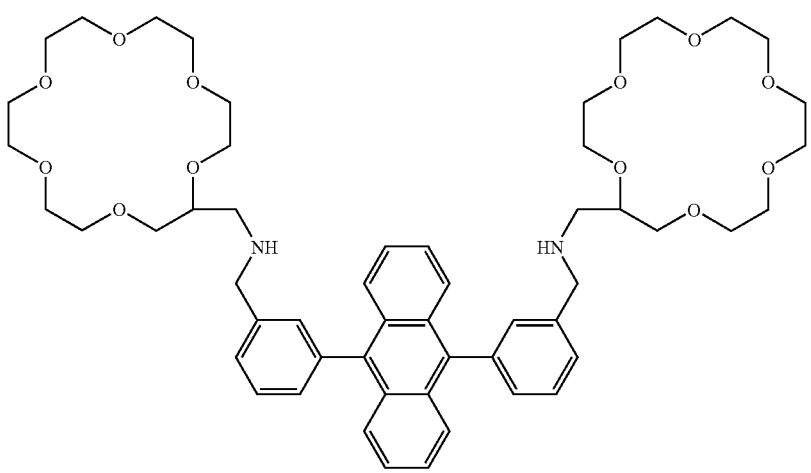

3

Similarly, in other embodiments, the modulating agent may be formed by derivitizing any of the three components with one or more receptors that bind analytes. Compounds 2 and 3 below are derivatives of DPA, a chromophore, having receptors designed to bind with metal ions. In these designs, the fluorescence may be quenched in the absence of metal ions due to photo induced electron transfer (PET) to the dye molecule from the neighboring N or O lone electrons. This PET mechanism has a quenching effect on the CIEEL pathway, which may result in a lack of observable chemiluminescence. In the metal bound state, N or O lone electrons may be unavailable for PET quenching such that the CIEEL pathway may be "turned on" to generate chemiluminescence.

Another example of a derivatized chromophore that may bind an analyte may comprise a chromophore, such as DPA, and a boronic acid group. In certain embodiments, chromophores derivatized with a boronic acid group may be used to sense or detect α-hydroxy carboxylic acids. For example, a chemiluminescent receptor 4 may be designed for the sensing of tartaric acid. In the tartrate unbound state, fluorescence may be quenched due to PET from the nitrogen lone pair electrons, where as in the presence of tartrate the chemiluminescence signal may be turned on.

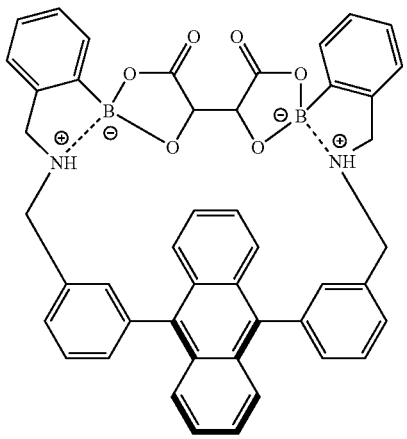

4

This same boronic acid receptor also may be used for the chemiluminescent sensing of sugars (compound 5).

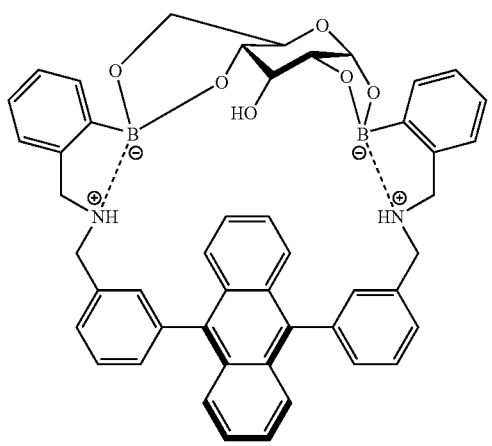

In general, the POCL chemiluminescence of the present disclosure will involve having one or more of the CL reaction components present in a liquid phase. The liquid phase may be solvent that is chosen to enhance CL. Such solvents generally support the solubility of the oxalate and/or chromophore, and generally should not completely quenching the CL. Suitable solvents include aprotic solvents, for example, ester solvents (e.g., phthalate solvents) and nitrile solvents (e.g., acetonitrile). In certain embodiments, the oxalate and solvent may be combined, for example, an ester solvent that comprises an oxalate.

In certain embodiments, the POCL chemiluminescence of the present disclosure may be effected on a substrate, such as for example, a solid support. Such embodiments may be useful for, among other things, to form a sensor that detects an analyte. Accordingly, the present disclosure also provides, according to certain embodiments, compositions comprising one or more of a chromophore, an oxalate ester, a peroxide, a modulating agent, and an optional analyte (collectively referred to as the CL reaction components). In such embodiments, any combination of CL reaction components may be associated with a substrate using methods known in the art. For example, the substrate be formed only from CL reaction components or it may comprise additional components.

In one embodiment, the CL reaction components form a substrate. Such substrates may be formed into a film comprising, for example, a chromophore and an oxalate ester. In this way, the CL reaction components may be provided without the need for a solvent. Film substrates may be formed, for example, by combining an oxalate ester and chromophore into a dichloromethane solution of polystyrene-co-acrylonitrile with subsequent evaporation into a film. These substrates may be applied to a variety of surfaces and used in a variety of applications, for example, they may be placed on a surface to form a sensor for detecting an analyte.

Figure 3:
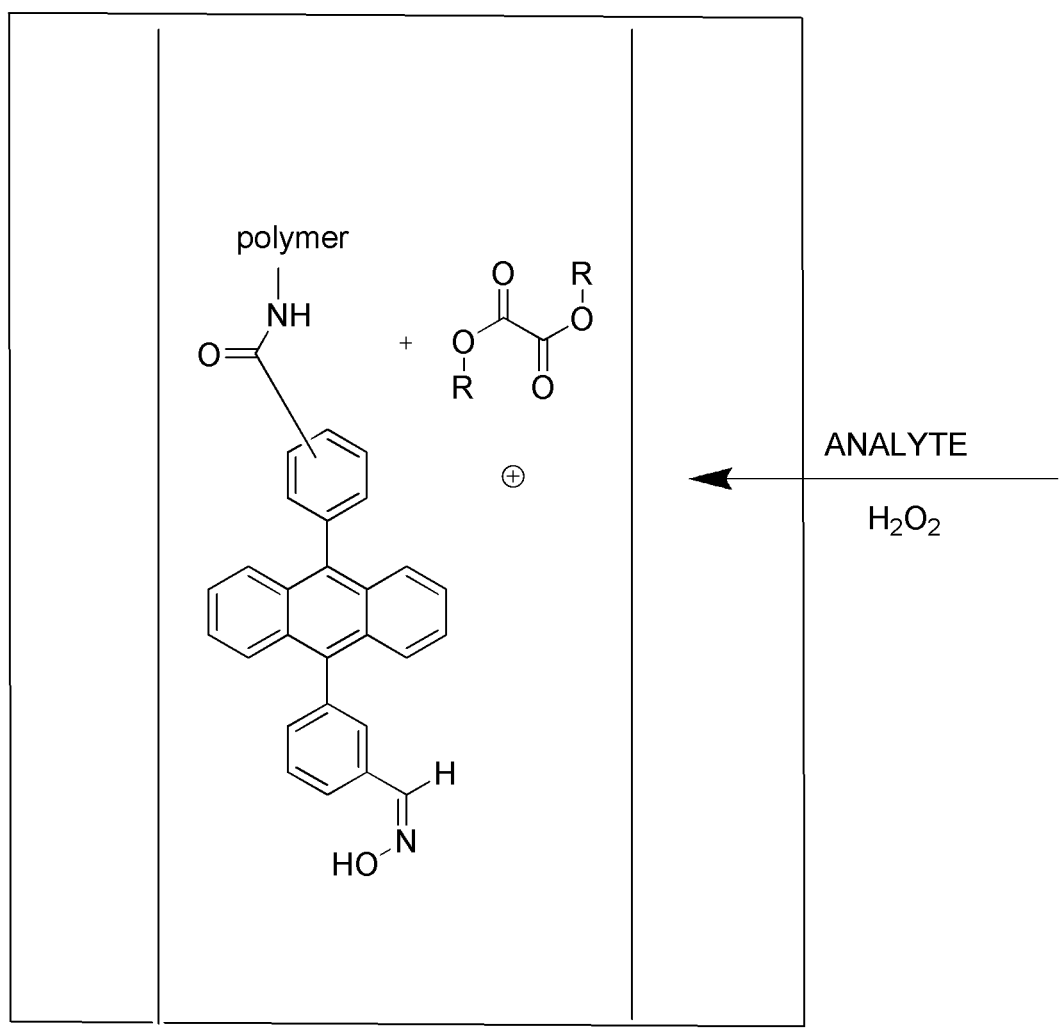
FIG. 3 depicts a lateral flow membrane example embodiment.

In another embodiment, a substrate may be combined with one or more of the CL reaction components. In one example, the substrate may be a lateral flow membrane. The CL reaction components may be incorporated onto the lateral flow membrane using any suitable technique, for example, using peptide chemistry. Upon introduction of an analyte, the reaction is triggered and the lateral flow test gives off a positive chemiluminescent signal (see FIG. 3). Other substrates also are suitable, depending on the particular application, for example, paper, swabs, adhesive strips, labels, and the like.

The present disclosure also provides, according to certain embodiments, using ink jet printing to print a pattern on a substrate, the pattern comprising one or more CL reaction components. Ink jet printing may be used to print any pattern on any substrate suitable for printing with an ink jet printer. Example of suitable substrates for printing include, but are not limited to, paper, transparent films, card stock, labels, adhesives films, dual sided adhesive films, chromatography paper, filter paper, gelled films, and the like.

In general, the ink jet cartridges used for printing are loaded with CL reaction components depending on the application and desired outcome. For example, the ink jet cartridges may be loaded with chromophore, an oxalate ester, a modulating agent, and a solvent, which may comprising additional components, that support solubility of the CL reaction components, for example, solvents and components that support the solubility of the CL components without adversely affecting the ink jet cartridge. Examples of suitable solvents include, but are not limited to, alcohols such as methanol, ethanol, propanol and butanol, and glycols such as propylene or ethylene glycol. An example of a solvent comprising additional components is an aqueous solution with one or more viscosifying agents, such as a surfactant, gelling agent, or suspended colloid.

After printing a substrate with such cartridges, the printed pattern can be exposed to an analyte mixture, then developed by exposing the substrate to a peroxide (e.g., by using a solution containing a peroxide). In another example, one or more of the CL reaction components may be present in the substrate before printing.

In one specific example, one or more of the CL reaction components were printed as the text "Texas." This print was exposed to a mist of hydrogen peroxide. The text glowed for about 30 seconds. One skilled in the art would recognize that the length of the glow is concentration dependent upon the one or more of the CL reaction components printed and the amount printed. For example, most inkjet printers permit the user to select the amount of ink deposited indirectly from choosing the print quality. Generally speaking, the slower the print speed, and the higher the quality of print the more 'ink' is deposited.

The methods of the present disclosure may be used in numerous other embodiments to modulate light output. For example, different chromophores or combinations of chromophores may be used to change the observed color resulting from the chemiluminescent reaction. In certain embodiments, one or more of the three components may be generated via a reaction that may be responsive to the presence of an analyte. For example this peroxyoxalate chemiluminescence (POCL) can be used for trace determination of hydrogen peroxide, most commonly in environmental and clinical analysis. Carbomate and organophosphorous compounds release hydrogen peroxide in their mechanism of action. Accordingly, these pesticides may be detected using the signaling technology of the present disclosure. In certain embodiments, an oxalate sensor using plant tissues as the source of oxalate oxidase may be utilized. The technology of the present disclosure may also be useful in enzymatic chemiluminescent and bioluminescent detections, DNA analysis with microtiter plate, and fiber optic chemiluminescence immunosensors. In certain embodiments, the compositions and methods of the present disclosure may be combined with existing assays that utilize antibodies and/or aptamers. There may be a huge potential that this signaling technology can widely be used in detecting large number of variety of analytes.

In certain embodiments, the modulating agent may be a metal catalyst utilized to generate a chromophore for participation in the POCL mechanism. For example, a chromophore may be generated as the product of an assay for sensing ketones and aldehydes via a competitive process between the desired analyte and a palladium(II) catalyst for a dithiol "host". This competition is described in Scheme 4 below.

Scheme 4:

Details of the recognition element in the Suzuki based signal amplification of ketone/aldehyde detection. The carbonyl is first condensed with the dithiol to form the 1,3-dithiolane 2. Then the remaining thiol is used to poison a portion of the palladium catalyst.

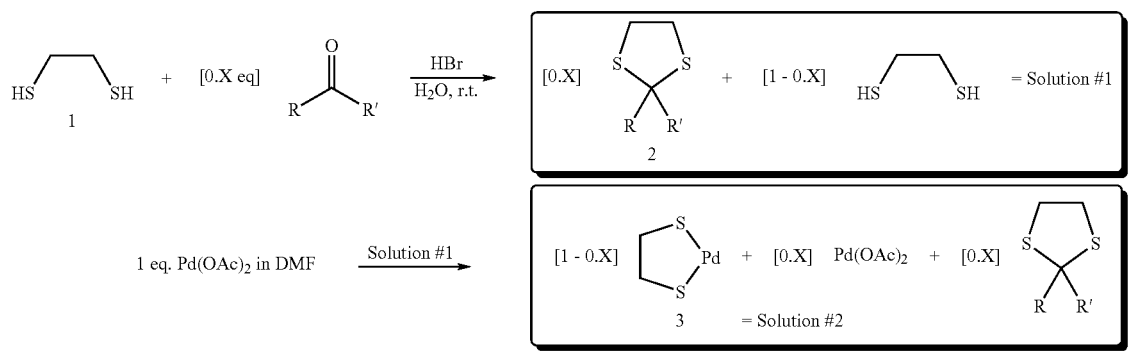

Using conventional dithiolane protection chemistry, a variable amount of the carbonyl analyte may be condensed with a set quantity of 1,2-ethanedithiol in water with catalytic hydrogen bromide to yield the 1,3-dithiolane product 2 and the remainder of free 1,2-ethanedithiol. This solution may be basified upon completion to deprotonate the immiscible dithiol and create a homogeneous solution. In a separate reaction vessel, a known concentration of palladium (II) acetate may be placed in dimethyl formamide. To this vessel, an aliquot of the basic 1,2-ethanedithiol solution may be added such that the total molar concentration of dithiol, both condensed and free, is equal to that of the palladium catalyst. Any free dithiol, may chelate the palladium and poison it for use in the Suzuki cross-coupling reaction to follow. The condensed dithiol may not interact with the palladium acetate, thereby leaving a portion of the total palladium free to catalyze the reaction of Scheme 5 below.

Scheme 5:

Palladium acetate in the presence of sodium carbonate in a water/DMF mixture, catalyzes the Suzuki cross-coupling reaction very efficiently. Product 5 is highly fluorescent and chemiluminescent. Compound 6 is used as an internal standard.

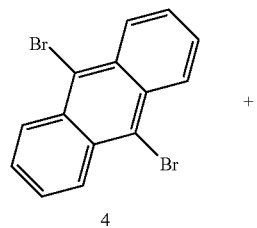

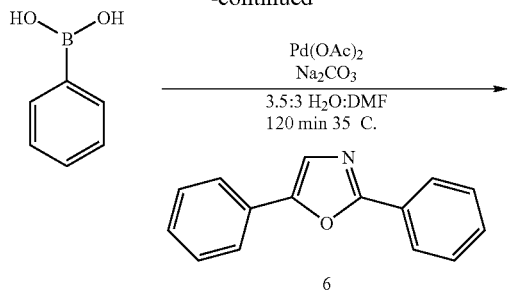

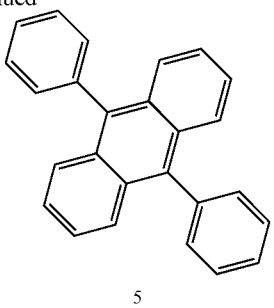

The signal output target 9,10-diphenylanthracene, compound 5, may be chosen for its favorable optical and synthetic properties. It has a fluorescence quantum efficiency of 1.0, a CIEEL chemiluminescence efficiency of nearly 0.8, and a one step catalytic synthesis from compound 4 (9,10-dibromoanthracene), a much less fluorescent and chemiluminescent precursor. The Suzuki cross-coupling reaction conditions may be adapted from the literature, and 2,5-diphenyloxazole may be present as an internal fluorescent standard. Liu, Leifang; Zhang, Yuhong; Xin, Bingwei *J. Org. Chem.*, 2006, 71(10), 3994-3997. The rate of formation of compound 5 may vary according to the amount of remaining free catalyst. Hence, the rate of the Suzuki reaction is theoretically directly proportional to the concentration of carbonyl analyte.

Figure 2:
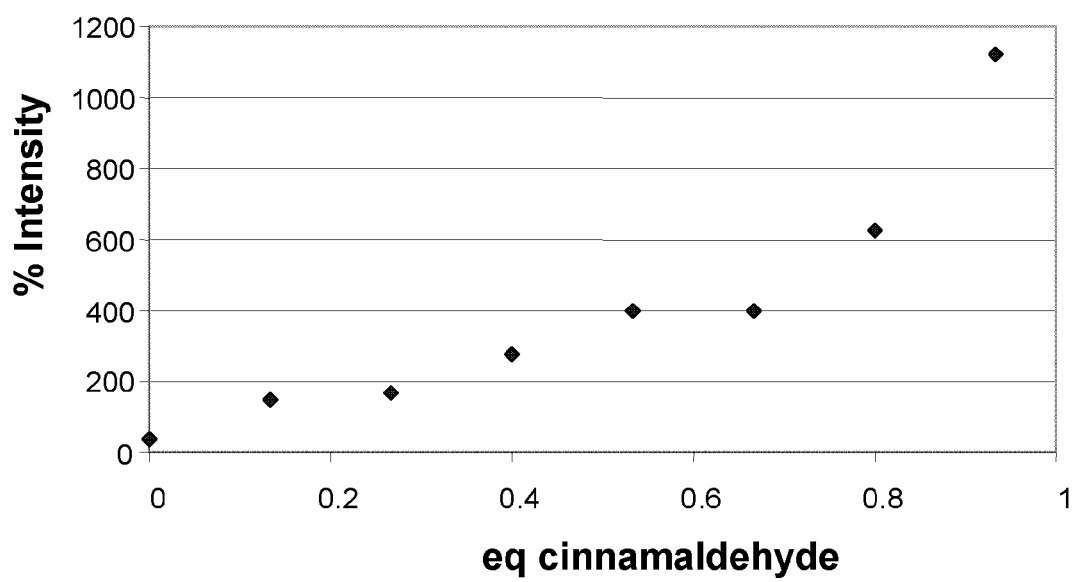
FIG. 2 depicts the rate profile of the chemiluminescence increase after a 120 minute reaction time for the palladium catalyzed generation of a chromophore.

The foregoing assay may be conducted in two parallel reaction vessels. One flask serves as the control for a time zero measurement, and the second may be allowed to react for two hours before quenching. Both flasks contain all reagents except the control flask lacks the phenylboronic acid. The samples are taken by extracting the solutions with equal amounts of ethyl acetate and diluting to an acceptable level for fluorescence measurements. No further workup is required. The charts in FIG. 1 show the increase in signal output from time zero to 120 minutes versus the equivalents of analyte cinnamaldehyde. FIG. 1 shows the increase in fluorescence whereas FIG. 2 is the increase in chemiluminescence. Chemiluminescence measurements were taken using the undiluted extract in a fluorometer with the excitation source shuttered using CIEEL initiation. Chemiluminescence may be roughly 7 times more sensitive than fluorescence for this assay.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition consisting essentially of:
   a chromophore, wherein the chromophore comprises at least one chromophore selected from the group consisting of rubrene, 9,10 bis(phenylethynyl)anthracene, 1,8-dichloro-9,10 bis(phenylethynyl)anthracene, anthracene, and an anthracene derivative;
   an oxalate ester, wherein the oxylate ester comprises at least one oxalate ester selected from the group consisting of bis(2-carboxypentyl oxy-3,5,6 trichlorophenyl) oxalate, bis(2,4,6-trichlorophenyl)oxalate, bis(pentafluorophenyl)oxalate, bis(2,4-dinitrophenyl)oxalate, and bis(2,4,6-trinitrophenyl)oxalate;
   a peroxide, wherein the peroxide comprises at least one peroxide selected from the group consisting of 2,4-pentanedione peroxide, 2-butanone peroxide, ammonium persulfate, barium peroxide, benzoyl peroxide, calcium peroxide, dicumyl peroxide, di-tert-amyl peroxide, hydrogen peroxide, a hydrogen peroxide-urea adduct, lauroyl peroxide, lithium peroxide, magnesium peroxide, nickel peroxide, a nickel(II) peroxide hydrate, tetrabutylammonium salt, a phosphate-citrate buffer with sodium perborate, a phosphate-citrate buffer with urea hydrogen peroxide, potassium peroxodisulfate, potassium persulfate, sodium perborate monohydrate, sodium perborate tetrahydrate, sodium peroxide, sodium persulfate, strontium peroxide, tert-butyl peroxide, area hydrogen peroxide, and zinc peroxide;
   a modulating agent, wherein the modulating agent consists essentially of an oximate that preferentially reacts with an analyte rather than the oxalate ester; and
   the analyte,
   wherein the oxalate ester preferentially reacts with the peroxide rather than the modulating agent in the presence of the analyte to form a peroxyoxalate intermediate, which reacts with the chromophore to produce a chemiluminescent signal.

2. The composition of claim 1, wherein the analyte comprises a chemical warfare agent.

3. The composition of claim 1, wherein the analyte comprises sarin.

4. The composition of claim 3, wherein the analyte comprises soman.

* * * * *